US00PP27870P2

(12) United States Plant Patent
Zaiger et al.

(10) Patent No.: US PP27,870 P2
(45) Date of Patent: Apr. 11, 2017

(54) PEACH TREE NAMED 'SWEET AURORA'

(50) Latin Name: *Prunus persica*
Varietal Denomination: Sweet Aurora

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 14/998,627

(22) Filed: Jan. 28, 2016

(51) Int. Cl.
*A01H 5/08* (2006.01)

(52) U.S. Cl.
USPC ..... Plt./197

(58) Field of Classification Search
USPC ..... Plt./197
See application file for complete search history.

*Primary Examiner* — Annette Para

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size, yellow flesh fruit.
3. Fruit with very good flavor and eating quality, mild, sweet and low acid.
4. Fruit being relatively uniform in size throughout the tree.

1 Drawing Sheet

Botanical designation: *Prunus persica.*
Variety denomination: 'Sweet Aurora'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

Prior Varieties

Among the existing varieties of peach trees, which are known to us, and mentioned herein, 'Spring Treat' Peach (U.S. Plant Pat. No. 12,419) and the proprietary non-patented peach seedling selections '214LP37', '214LK573', '57ZA266' and '174LE143'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between our proprietary non-patented peach seedlings '214LP37' and '214LK573'. The seed parent (214LP37) originated as an open pollinated seedling from seed of our proprietary non-patented peach seedling selection '57ZA266'. The pollen parent (214LK573) originated from seed of our proprietary non-patented peach seedling selection '174LE143'. A large number of these first generation seedlings were planted and grown on their own root system. Under close and careful observation we recognized the desirable tree and fruit characteristics of the present seedling and selected it in 2010 for additional asexual propagation and commercialization.

ASEXUAL REPRODUCTION OF THE VARIETY

In 2010 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a regular and productive bearer of large size, yellow flesh, clingstone fruit with very good flavor and eating quality. The fruit is further characterized by having an attractive dark red skin color and being relatively uniform throughout the tree. In comparison to its non-patented peach seed parent '214LP37' the fruit of the new variety has firmer flesh and is approximately 7 days earlier in maturity. In comparison to its non-patented peach pollen parent '214LK573' the fruit of the new variety is larger in size and is approximately 6 days later in maturity. In comparison to the commercial variety 'Spring Treat' Peach (U.S. Plant Pat. No. 12,419) the fruit of the new variety is larger in size, has firmer flesh and is approximately 3 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies slightly with type and fertility of soil, climatic conditions and cultural practices.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 3 consecutive years. No alternate bearing observed.

*Fertility*.—Self fertile.

*Density*.—Medium dense, usually pruned to vase shape to increase air movement and sunlight to center of tree to enhance fruit color and health of fruit wood.

*Hardiness*.—Hardy in all stone fruit growing areas of California. Tree grown in USDA Hardiness Zone 9. Winter chilling requirement approximately. 650 hours at or below 45° F.

Trunk:

*Size*.—Large, average circumference 55.9 cm at 27.9 cm above ground on a 5 year old tree.

*Stocky*.—Medium stocky.

*Texture*.—Medium shaggy, roughness increases with age.

*Color*.—Varies from 2.5YR 5/2 to 5Y 4/2.

Branches:

*Size*.—Medium. Average circumference 16.3 cm at 1.2 meters above ground. Crotch angle approximately 30°, increases with heavy crop load.

*Surface texture*.—New growth relatively smooth. Mature growth medium rough, roughness increases with age of tree.

*Lenticels*.—Average number 23 in a 25.8 square cm area. Average length 5.1 mm. Average width 2.4 mm. Color varies from 7.5YR 6/10 to 7.5YR 5/10.

*Color*.—New growth varies from 2.5GY 6/6 to 5GY 6/6. Mature growth varies from 10YR 4/6 to 7.5YR 4/6, varies with age of growth.

Leaves:

*Size*.—Medium to large. Average length 152.5 mm. Average width 36.6 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Large. Average length 11.7 mm. Average width 1.7 mm. Longitudinally grooved. Surface — glabrous. Color varies from 2.5GY 4/6 to 5GY 4/8.

*Glands*.—Type — reniform. Size — medium. Average length 1.3 mm. Average diameter 0.8 mm. Number varies from 3 to 5, average number A. Located primarily on the base of the leaf blade and upper portion of petiole. Color varies from 10R 3/4 to 10YR 4/4.

*Stipules*.—None present at time of measurement.

*Color*.—Upper surface varies from 5GY 3/4 to 7.5GY 2/4. Lower surface varies from 7.5GY 4/4 to 7.5GY 3/4. Midvein color varies from 2.5GY 6/4 to 5GY 6/4.

Flower buds:

*Size*.—Large. Average length 21.3 mm. Average diameter 10.9 mm.

*Hardiness*.—Hardy with respect to California winters.

*Density*.—Dense.

*Form*.—Conical, becoming elongated just before opening.

*Pedicel*.—Medium. Average length 6.0 mm. Average width 1.2 mm. Surface- glabrous. Color varies from 5GY 8/8 to 7.5GY 6/10.

*Color*.—Varies from 5RP 8/6 to 7.5RP 6/12.

Flowers:

*Blooming period*.—Date of First Bloom Feb. 11, 2015. Date of Petal Fall Feb. 21, 2015, varies slightly with climatic conditions.

*Size*.—Large. Average height 21.6 mm. Average diameter 47.0 mm.

*Petals*.—Normally 5, alternately arranged to sepals. Size — large. Average length 21.4 mm. Average width 18.9 mm. Form — orbicular. Margin — sinuate. Arrangement — overlapping. Petal apex — rounded. Petal base — truncate. Color varies from 5RP 9/2 to 5RP 8/6, fades with age of flower. Both upper and lower surfaces glabrous.

*Sepals*.—Normally 5, alternately arranged to petals. Size — large. Average length 7.3 mm. Average width 6.9 mm. Shape — ovate. Apex — rounded to triangular. Surface — upper surface glabrous, lower surface pubescent. Color — upper surface varies from 7.5GY 6/10 to 7.5GY 6/12. Lower surface varies from 7.5RP 4/12 to 7.5RP 3/10.

*Stamens*.—Average number per flower 52. Average filament length 15.4 mm. On average, the stamens are above the height of the petals. Filament color N 9.5/(white). Anther color varies from 7.5R 4/12 to 5Y 8/10.

*Pollen*.—Self fertile. Color varies from 2.5Y 7/12 to 5Y 7/12.

*Pistil*.—Number — normally one. Average length 19.1 mm. Surface — pubescent. Position of stigma an average of 1.1 mm below anthers. Color varies from 2.5GY 8/6 to 2.5GY 7/8.

*Fragrance*.—Wanting.

*Color*.—Varies from 7.5RP 9/2 to 7.5RP 8/6.

*Pedicel*.—Average length 4.6 mm. Average width 1.4 mm. Surface — glabrous. Color varies from 7.5GY 8/8 to 7.5GY 6/12.

*Number flowers per flower bud*.—Normally one.

Fruit:

*Maturity when described*.—Firm ripe and ready for consumption.

*Date of first picking*.—May 25, 2015.

*Date of last picking*.—Jun. 4, 2015, varies slightly with climatic conditions.

*Size*.—Large. Average diameter axially 71.0 mm. Average transversely in suture plane 76.2 mm. Average weight 252.8 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Slightly retuse.

*Base*.—Retuse.

*Stem cavity*.—Rounded to slightly elongated in suture plane. Average depth 8.2 mm. Average diameter 7.4 mm.

Stem:

*Size*.—Small to medium. Average length 8.7 mm. Average diameter 3.6 mm.

*Color*.—Varies from 5GY 5/6 to 5GY 5/8.

Flesh:

*Ripens*.—Evenly.

*Texture*.—Firm, meaty.

*Fibers*.—Few, small, tender.

*Firmness*.—Firm, comparable to other commercial peach varieties.

*Aroma*.—Moderate.

*Amydgalin*.—Undetected.

*Eating quality*.—Very good.

*Flavor*.—Very good, mild, sweet, low acid.

*Juice*.—Heavy amount, enhances flavor.

*Acidity*.—Not available.

*Brix*.—Average Brix 13.1°, varies slightly with amount of fruit per tree and climatic conditions.

*Pit cavity*.—Average length 36.9 mm. Average width 27.2 mm. Average depth 11.3 mm. Varies from 5Y 8/8 to 5Y 7/6.

*Color*.—Varies from 5Y 8/6 to 5Y 8/8.

Skin:

*Thickness*.—Medium.

*Surface*.—Smooth.

*Pubescence*.—Moderate amount, short in length.

*Tendency to crack*.—None.

*Color*.—Ground color varies from 5Y 8.5/6 to 5Y 8/6. Overspread with 7.5R 3/10 to 7.5R 2/4.

*Tenacity*.—Tenacious to flesh.

*Astringency*.—Slight to none.

Stone:

*Type*.—Clingstone, strong adherence to flesh.

*Size*.—Large. Average length 35.9 mm. Average width. 26.2 mm. Average thickness 20.5 mm.

*Form*.—Obovoid.

*Base*.—Flat.

*Apex*.—Rounded.

*Surface*.—Pitted throughout, pits vary from rounded to elongated.

*Sides*.—Unequal, one side extending further from suture plane.

*Ridges*.—Small, narrow ridge extending from base toward apex.

*Tendency to split*.—None.

*Color*.—Varies from 7.5YR 6/6 to 10YR 6/6 when dry.

Kernel:

*Size*.—Large. Average length 19.7 mm. Average width 11.0 mm. Average depth 6.2 mm.

*Form*.—Ovoid.

*Viability*.—Partially viable, some embryos with incomplete development.

*Skin color*.—Varies from 5Y 9/4 to 7.5Y 9/4.

Use: Dessert.

*Market*.—Local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, substantially as illustrated and described.

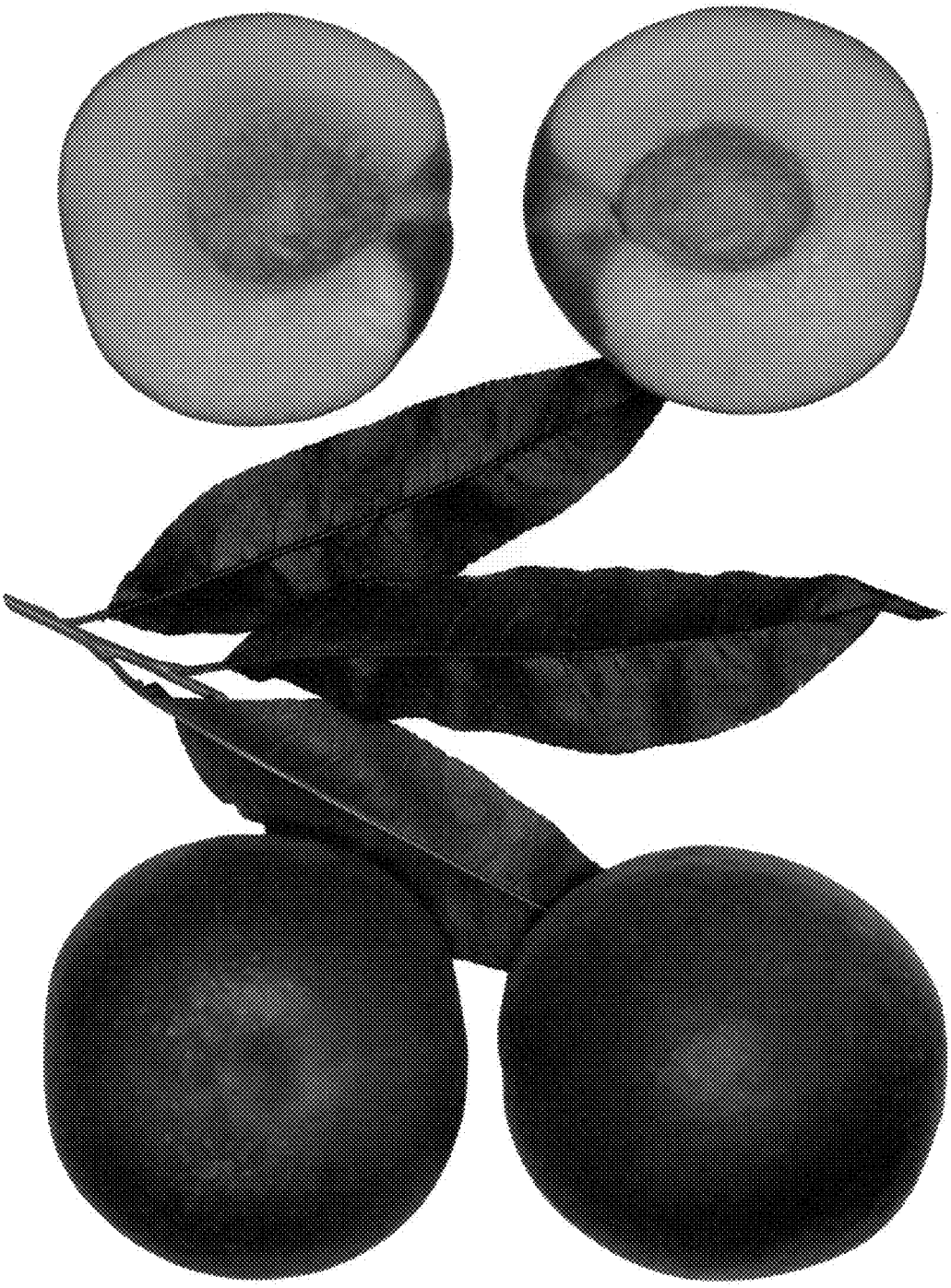

* * * * *